US00PP08640P

United States Patent [19]

Hosage, Jr.

[11] Patent Number: Plant 8,640

[45] Date of Patent: Mar. 15, 1994

[54] TEXAS REDBUD TREE NAMED TRAVELLER

[76] Inventor: Daniel A. Hosage, Jr., 2318 Hilliard Rd., San Marcos, Tex. 78666

[21] Appl. No.: 943,447

[22] Filed: Sep. 10, 1992

[51] Int. Cl.[5] ..... A01H 5/00

[52] U.S. Cl. ..... Plt./51.1

[58] Field of Search ..... Plt. 51.1, 54.1

[56] References Cited

PUBLICATIONS

Huxley, A., et al., (Eds.), "Cercis" *The New Royal Horticultural Society Dictionary of Horticulture* vol. I 1992 The Stockton Press, N.Y. pp. 573-574.

Vines, R. A., "Legume Family" *Trees, Shrubs, and Woody vines of the Southwest* 1984 University of Texas Press, pp. 553-555.

Krüssmann, G., "Cercis" *Manual of Cultivated Broad--Leaved Trees and Shrubs* 1976 Timber Press, Beaverton, Org., pp. 311-313.

Hopkins, M., (1942) "*Cercis* in North America" *Rhodora,* vol. 44, No. 522, pp. 193-211.

*Primary Examiner*—James R. Feyrer

*Attorney, Agent, or Firm*—Gunn, Lee & Miller

[57] ABSTRACT

A variety of Texas Redbud (*Cercis canadensis* var. *texensis*) having alternating stem branching with the orientation of shoot tip growth approximately −45° from the horizon with occasional arching shoots eventually reorienting downward. The leaves are cauline, petiolate with petioles glabrous and terete. Emerging foilage is red in color.

4 Drawing Sheets

BACKGROUND OF THE INVENTION

The present invention relates to a new and distinct variety of Texas Redbud (*Cercis canadensis* var. *texensis*) which was discovered from selection of some 10,000 seedlings grown from seed obtained from a wild stand of *Cercis canadensis* var. *texensis* in Blanco County, Tex. The discovery has been entitled Texas Redbud Tree named "Traveller". The seedlings were grown in San Marcos, Hays County, Tex. Seed was collected in Blanco County in the state of Texas; specifically at the junction of the little Blanco River and U.S. 281. Seed was cleaned, scarified and germinated at a nursery located at 2318 Hillard Road in Hays County, Tex. Asexual propagation by both tip cuttings and by grafting were also done at the same location.

BRIEF SUMMARY OF THE INVENTION

This new variety of redbud is best taxonmically referable to variety *texensis* by the following considerations:

(1) the mature adaxial leaf surface is glaucous with leaf color deep green, and leaf blade texture coriaceous;

(2) the leaf tip is emarginate with the leaf margin slightly undulate; and (3) the petiole glabrous.

These features delineate the new variety from either variety *canadensis* or variety *mexicana.*

The plant is characterized by its shoot tip growth orientation of approximately −45° from the horizon with occasional arching shoots reorienting downwardly.

BRIEF DESCRIPTION OF THE DRAWINGS

Sheet 1 is a photograph of the new and distinct variety showing the steam alternate branching and the orientation of arching shoots reorienting downwardly.

Sheet 2 is a photograph of the new and distinct variety showing the leafing and weeping habit.

Sheet 3 is a photograph of the new and distinct variety showing the leaf color with margins slightly undulated.

Sheet 4 is a photograph of the new and distinct variety of Texas redbud, showing a branch of a typical specimen in full bloom, the angle of twigs from the stem, the bark coloration, and the early leaf characteristics of this plant.

BOTANICAL DESCRIPTION OF THE PLANT

The selection is currently being asexually reproduced by tip cuttings. New, green growth from stem tips 3 nodes long, are dipped in 0.3% IBA and set in a mist room. Callus forms within forty (40) days, followed by root formation at sixty (60) to seventy-five (75) days. Approximately seventy-five (75%) percent of the cuttings take.

The metric system is used for measurements and all terms are in accordance with standard botanical nomenclature. Measurements were taken from the original selection grown in full sun. The plant was well watered and fertilized.

Propagation

Micropropagation in tissue culture will most likely be the mode of commercial reproduction. This species and variety is already being successfully micropropagated by at least 2 commercial tissue culture labs in the United States. Whether micropropagation will be "in house" and done at this location or will be farmed out is uncertain at this time.

This plant has been successfully propagated by tip cutting and by grafting. The plant has been shown to graft successfully to all three varieties of the eastern redbud. Attempts have not been made at grafting to any of the other 5 species of Cercis.

The plant is to be marketed as a "standard" for use as a ground cover, potted specimen, use on terraces, and the like, as well as use as a bonsai subject. Grafted uses on tall tree form stock to form weeping specimens at fixed heights (for example at 3', 5', 7') are also intended.

All members of the variety texensis show anthocyanin-tinted new growth—hence this is not unique to this discovery.

Plant

The plant is a deciduous, unarmed, single-to-multi-trunked woody tree from at least −1.0 meters to at least 0.5 meters tall from multiple spreading, woody roots. The roots are smooth, light gray, with bark marked occasionally with bands of lenticels.

A. Stems: The stems are terete. The stem bark is smooth, marked by bands of elliptical lenticels, red-brown in color maturing to gray. Branching is alternate with orientation of shoot tip growth approximately −45° from horizon with occasional arching shoots eventually reorienting downward in a "weeping" habit.

B. Leaves: The leaves are cauline, petiolate with petioles glabrous and terete. Leave length is in the range of 1.8 cm to 4.0 cm with the average being 2.0–3.5 cm. The bases are pulvinal and the petiole junction with the leaf blade is apparent. The petiole color is yellow-green going to yellow at maturity and turning brown prior to abscission of the leaf. The leaf scar is elliptical in outline, 0.8–1.2 mm wide by 1.5–2.5 mm long. Stipules are present and abruptly deciduous, length 2.0–3.0 mm. width equal to less than 1.0 mm. There are two stipules per node. The leaves are simple, entire and alternate and distinctly coriaceous. The outline is reniform to somewhat cordate with margins entire and slightly undulate. The leaf apex is emarginate, occasionally rounded and rarely, slightly acute. The leaf base is reniform, sinus 1.5–5.0 cm broad with average being 2.0–3.5 cm to 0.8–1.8 cm deep with average being 1.0–1.3 cm. The leaf blades are (3.0−) 7.0–9.5 (−12.0) cm broad and (2.0−) 5.0–6.5 (7.5) cm long. The adaxial leaf surface is smooth and nitid at maturity with a deep green color and sunken veins. Emerging foilage is red in color. The abaxial surface is dull and light green in color with the veins raised with respect to the surface. The leaf orientation is reclinate and reclined. Major venation is apparent and palmate with 7–9 veins; minor venation is reticulate.

Reproductive Organs

The mother plant flowered for the first time in March of 1993. Flowers were typical of and substantially identical to that of all varieties of *C. canadensis.* Flower color was purplish-pink. No seed was set although this should not presume the plant to be sterile (less than 30 flowers were formed in a cold spring season with few pollinators).

In summary, the reproductive organs are substantially identical to the wild species forms. (See sheet 4 of the drawing).

Size and Vigor

The plant appears normal when compared with wild redbuds with exception of the weeping habit. A second year tip cutting (5" long original tissue) in a 15 gallon container has a height of 10–15" and a depth of 15–20"; spread being 24–36". Each branch appears capable of growing up to 18" per year under normal conditions. A depth of as much as 15" on a mature specimen with a spread of 18' (diameter) is projected; final height of 5' is projected. No reversions of buds to a true upright form has been observed. Occasional branches assume a more upright form for 5–8 leaves before reverting to the weeping form. Pruning requirements are unknown at this time.

The leaf arrangement is in minor contrast to the wild forms in that in the discovery the leaves are slightly imbricate and form two ranks on both sides of the descending branches. This results in a sheathing or shingled-by-leaves look peculiar to the discovery. In the wild form this imbricate nature is not expressed, even in branches with a forced descending orientation.

This plant has a characteristic weeping habit as compared to the wild types with leaves ascending. The result is a dramatic appearance.

Bark

Mature bark of wild Texas redbuds is uniformly smooth, grey and with occasional longitudinal furrows. As with other respects this feature is repeated in the discovery. Examination of several mature wild Texas redbuds (as well as the probable parent) shows mature bark to be grey—slate grey with patches lightening to ash grey. No brown color has been observed in any specimens examined nor has any checking of the bark into scales been observed (both characters of the eastern variety). Various lichens inhabit the bark surface of both the discovery and the wild form resulting in a mottled appearance.

I claim:

1. I claim a new and distinct variety of redbud, herein shown and described, characterized by its shoot tip growth orientation approximately −45° from the horizon with occasional arching shoots reorienting downwardly.

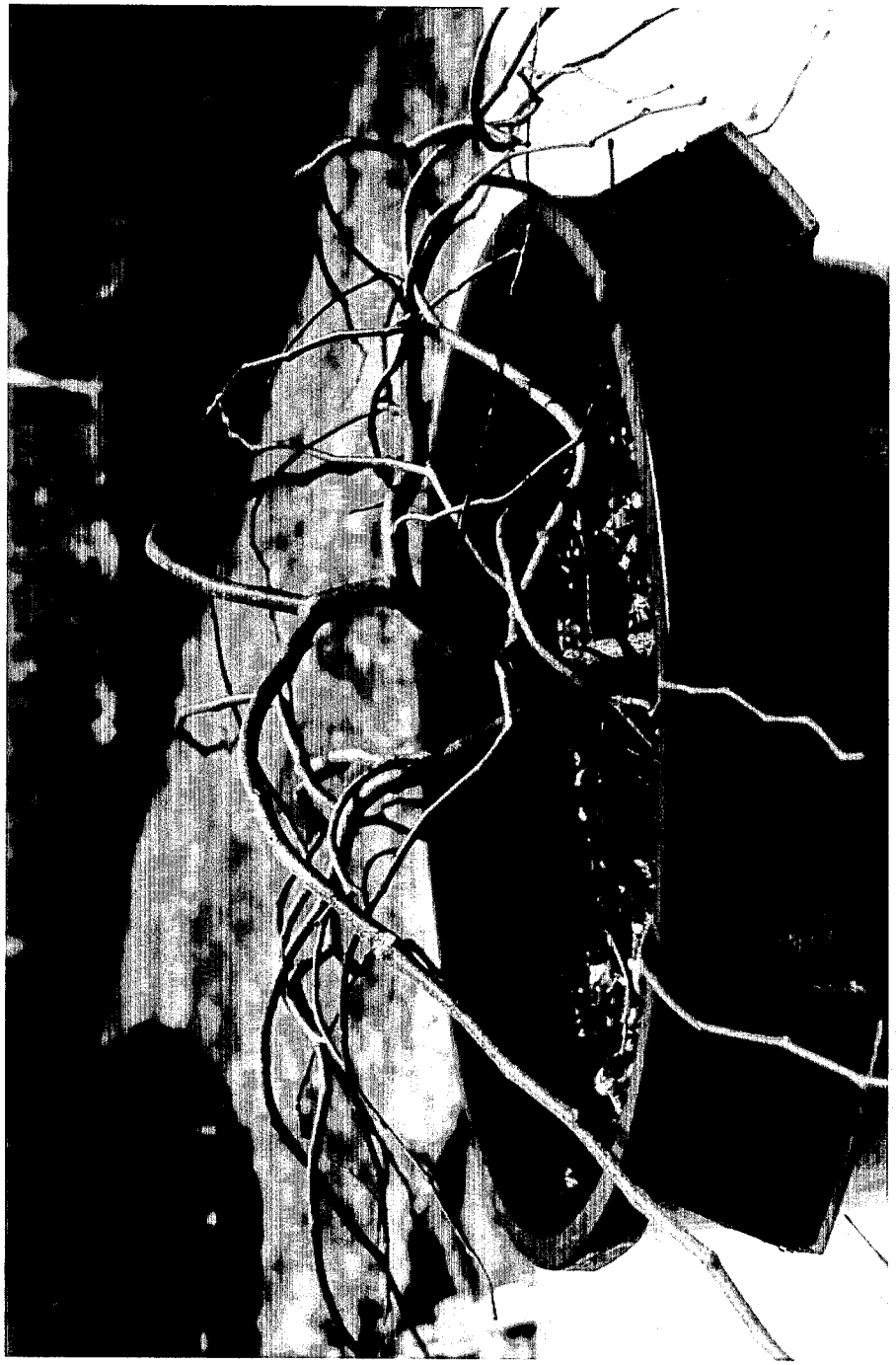

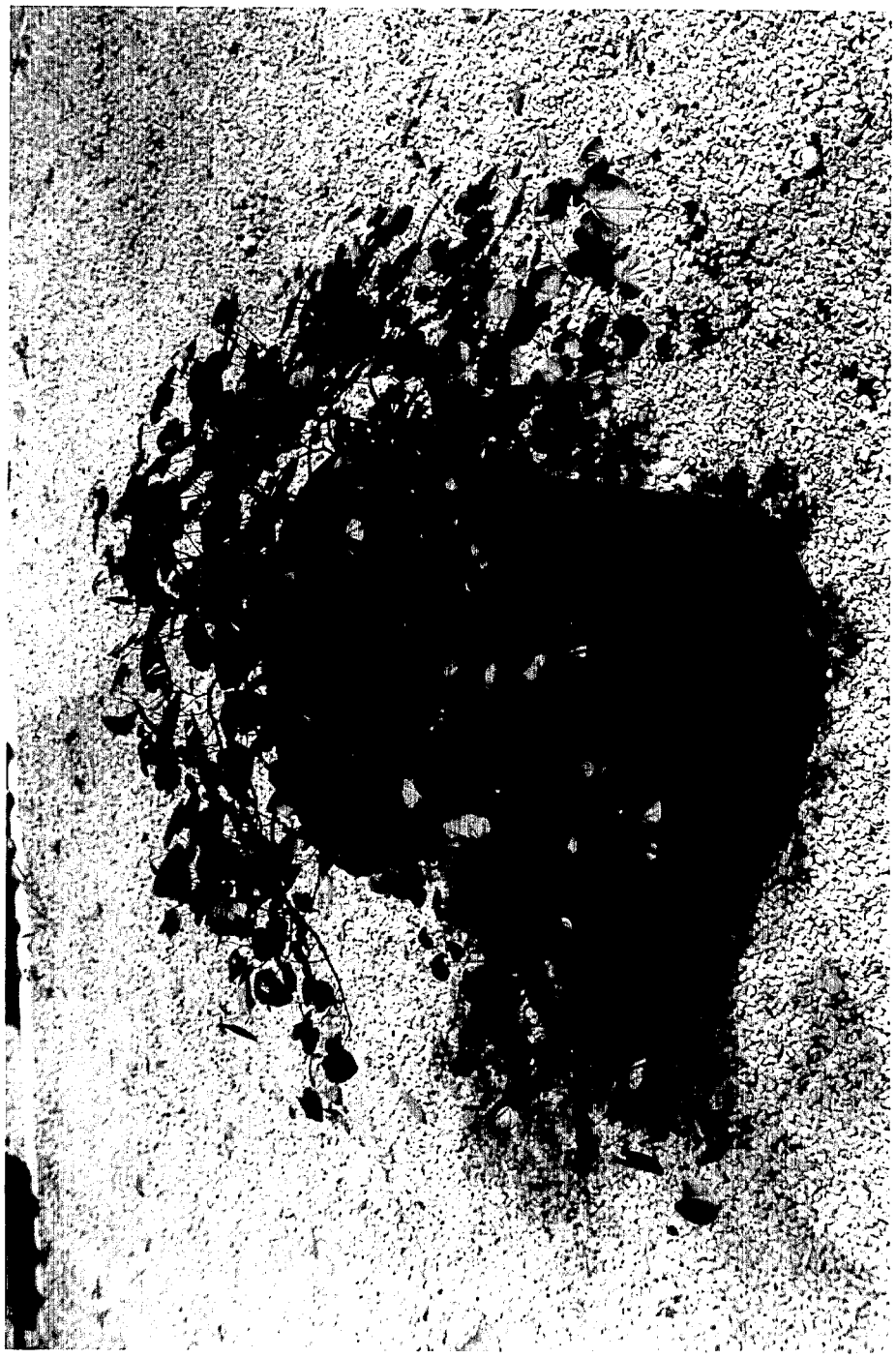

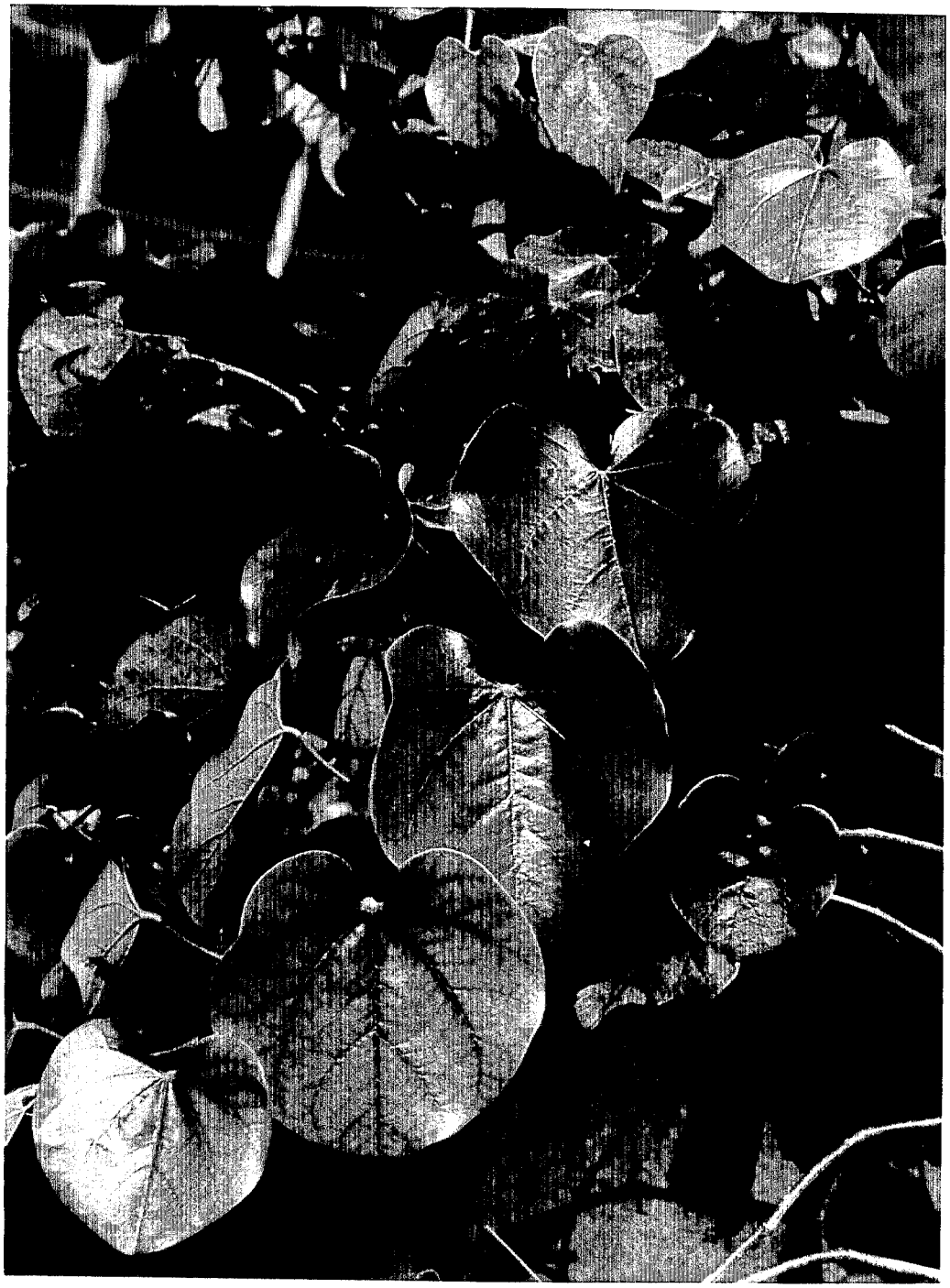

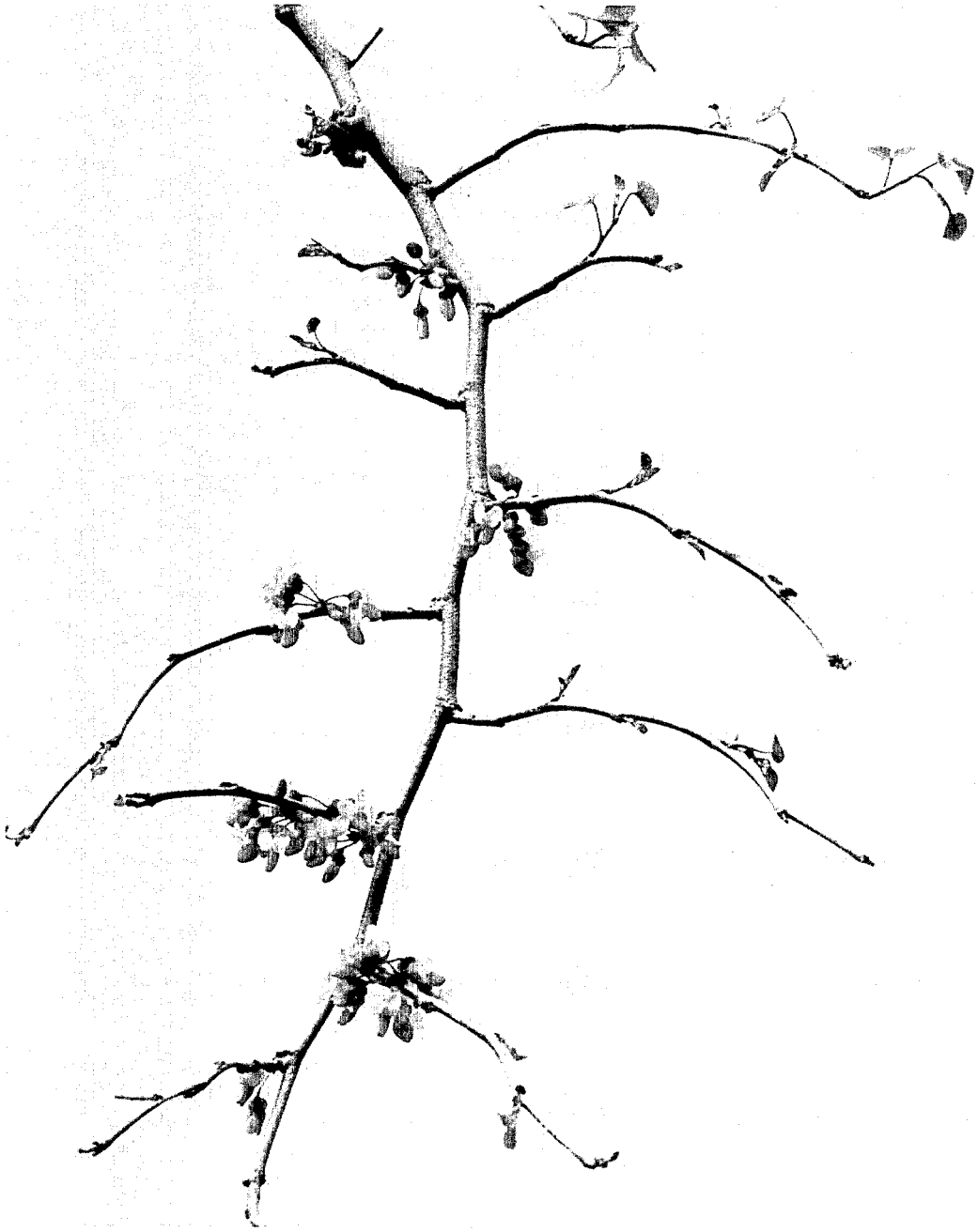

* * * * *